United States Patent [19]

Magee et al.

[11] 4,251,451

[45] Feb. 17, 1981

[54] PROCESS FOR PRODUCING A MIXTURE OF BRANCHED AND LINEAR CARBOXYLIC ACID SALTS

[75] Inventors: Walter L. Magee, Danbury, Conn.; Arthur C. Bayer, Yorktown Heights, N.Y.

[73] Assignee: Stauffer Chemical Company, Westport, Conn.

[21] Appl. No.: 106,979

[22] Filed: Dec. 26, 1979

[51] Int. Cl.$^3$ .................. C11C 1/00; C07C 51/295
[52] U.S. Cl. .................. 260/413; 562/539
[58] Field of Search .................. 260/413 R, 413 S; 562/539

[56] References Cited

U.S. PATENT DOCUMENTS

| | | | |
|---|---|---|---|
| 2,384,817 | 9/1945 | Chitwood | 260/413 X |
| 2,614,122 | 10/1952 | Mikeska | 260/413 X |
| 2,696,501 | 12/1954 | Stein | 260/413 X |
| 2,766,267 | 10/1956 | Hill | 260/413 |
| 3,121,728 | 2/1964 | Bartlett | 260/413 |
| 3,227,737 | 1/1966 | Ashworth | 260/413 |
| 3,365,476 | 1/1968 | Dimond | 260/413 |
| 3,370,074 | 2/1968 | Dimond | 260/413 X |
| 3,449,413 | 6/1969 | Hartel | 260/413 X |
| 3,503,896 | 3/1970 | Fishman | 260/413 X |
| 3,558,678 | 1/1971 | Fanning | 260/413 |
| 3,560,537 | 2/1971 | Eller | 260/413 |
| 3,657,293 | 4/1972 | Fanning | 260/413 |
| 3,671,581 | 6/1972 | Keenan | 260/413 X |
| 3,717,676 | 2/1973 | Bechara et al. | 260/413 X |
| 3,806,529 | 4/1974 | Havinga | 260/413 |
| 3,864,369 | 2/1975 | Isa et al. | 260/413 |
| 3,910,973 | 10/1975 | Isa et al. | 260/413 |
| 3,957,838 | 5/1976 | Nishino et al. | 260/413 X |
| 4,053,491 | 10/1977 | Koch et al. | 260/413 X |
| 4,144,183 | 3/1979 | Koch et al. | 260/410.6 |

OTHER PUBLICATIONS

Dumar and Stas, Ann, 35 129-173 (1840).

*Primary Examiner*—John F. Niebling
*Attorney, Agent, or Firm*—Michael E. Zall

[57] ABSTRACT

An improved process for reacting a mixture of branched and linear alcohols with a caustic, optionally in the presence of a catalyst, to produce a reaction mixture containing carboxylic acid salts, and to liberate hydrogen. The improvement comprises introducing into the reaction mixture at about a time when a significant evolution of hydrogen from the mixture begins to occur, an effective amount of an inert diluent for the reaction mixture. The effective amount is sufficient to maintain the fluidity of the reaction mixture. A preferred diluent is mineral oil. The improvement reduces the tendency of the reaction mixture to foam and solidify, thus permitting the reaction to proceed to completion and permitting the easy removal of the reaction mixture from the reaction zone. Additionally, the improvement insures that the branched and linear mixture of carboxylic acid salts produced substantially corresponds to the branched and linear mixture of alcohols reacted.

10 Claims, No Drawings

PROCESS FOR PRODUCING A MIXTURE OF BRANCHED AND LINEAR CARBOXYLIC ACID SALTS

BACKGROUND OF THE INVENTION

1. Field of the Invention

This invention relates to an improved process for producing a mixture of branched and linear carboxylic acid salts, in particular, an improved process which produces a reaction mixture having a reduced tendency to foam and solidify, thus permitting the reaction to proceed to completion and permitting the easy removal of the reaction mixture from the reaction zone. The process, additionally, insures that the branched and linear mixture of carboxylic acid salts produced substantially corresponds to the branched and linear mixture of alcohols reacted.

2. Prior Art

Carboxylic acid salts and acids derived therefrom are useful for the preparation of high quality bar soaps and other soap products, the preparation of various types of esters for various purposes such as lubricants, hydraulic fluids, edible oils and fats and numerous applications as intermediates in the preparation of a wide variety of chemical compounds. Mixtures of branched and linear carboxylic acids are particularly important for the production of the corresponding esters for use as lubricants or functional fluids, see U.S. Pat. Nos. 4,053,491 and 4,144,183 both to Koch et al.

The preparation of carboxylic acid salts and of carboxylic acids via the caustic fusion reaction of alcohols, with or without a catalyst, is a process that has been known for many years (see, for example, Dumas and Stas, Ann., 35, 129–173, 1840 and U.S. Pat. No. 2,384,817 to Chitwood). This process has of comparatively recent date become associated with the preparation of high purity salts and acids of a type capable of effective direct substitution for naturally derived salts and carboxylic acids in large use areas, such as manufacture of high quality soap products where cost is an important factor, and the production of esters for use in hydraulic fluids and lubricants. One possible reason for this is that it was only recently that synthetic alcohols of high purity and low cost became available in quantities sufficient for consideration as raw materials for the production of such salts and acids. Until this stage of technology was reached, the usual derivation of alcohols was from the acid components of ester materials in natural source oils and fats such as coconut oil. Thus, prior large scale processing was directed to producing alcohols from acid structures, not vice versa, and this for the most part made natural source derived alcohols more costly than natural source salts and acids; thus, there was no prior reason for considering large scale production of natural source type salts and acids from alcohols by a caustic fusion process or by any process for that matter.

The caustic fusion reaction of alcohols, i.e. reacting an alcohol (ROH) with a caustic M(OH)$_n$, to produce carboxylic salts, as indicated previously, is well known in the art, and various improvements on the process and variations thereof are described in, for example, the following U.S. Patents: U.S. Pat. No. 2,384,817 to Chitwood; U.S. Pat. No. 2,614,122 to Mikeska (which describes preparing dodecanedioic acid by cleaving 12-hydroxystearic acid with an alkali metal hydroxide in the presence of high boiling saturated petroleum hydrocarbons solvent resulting in a viscous emulsified mass which is difficult to purify); U.S. Pat. No. 2,696,501 to Stein; U.S. Pat. No. 2,847,466 to Steadmann et al (which describes a caustic fusion reaction in the presence of water); U.S. Pat. No. 3,121,728 to Bartlett; U.S. Pat. No. 3,227,737 to Ashworth; U.S. Pat. No. 3,365,476 to Dimond et al. (I); U.S. Pat. No. 3,370,074 to Dimond et al. (II); U.S. Pat. No. 3,449,413 to Hartel et al.; U.S. Pat. No. 3,503,896 to Fishman; U.S. Pat. No. 3,558,678 to Fanning (I); U.S. Pat. No. 3,560,537 to Eller; U.S. Pat. No. 3,657,293 to Fanning (II); U.S. Pat. No. 3,671,581 to Keenan; U.S. Pat. No. 3,717,676 to Bechara et al; U.S. Pat. No. 3,806,529 to Havinga et al; U.S. Pat. No. 3,864,369 Isa et al. (I); U.S. Pat. No. 3,910,973 to Isa et al. (II); and U.S. Pat. No. 3,957,838 to Nishino et al.

Generally, the known process (i.e. the caustic fusion reaction of alcohols) consists of reacting an alcohol of the formula RCH$_2$OH with a caustic of the formula M(OH)$_n$ to produce a reaction mixture containing the carboxylic acid salts of the formula:

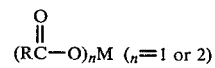

$$(RC-O)_nM \quad (n=1 \text{ or } 2)$$

wherein R is generally an alkyl substituent and M is an akali metal or an alkaline earth metal, usually sodium. The process liberates hydrogen.

The reaction may be carried out with or without a catalyst. Catalysts such as solid carbon, zinc, zinc oxide, cadmium, etc. have been used. The process may be accomplished under pressure or under atmospheric conditions and under varying temperature conditions.

Problems which have plagued this particular process are a tendency of the reaction mixture to foam, to form solid foams and to form a solidified reaction mixture. The foaming is generally caused by the agitation of the reaction mixture and the rapid liberation of hydrogen. This foaming can be extensive and cause the shutdown of the reaction. The formation of solid foams and a solid reaction mixture is probably due to the fact that the melting point of the carboxylic acid salts produced may be higher than the reaction temperature or higher than the temperature which the reaction mixture is cooled down to, for performance on the reaction mixture of a subsequent process step, e.g. acidification to carboxylic acid. Solid foam is probably formed when hydrogen, which is liberated from the reaction mixture, becomes entrapped in the solidifying reaction mixture. The solid foam and solidified reaction mixture make it extremely difficult to remove the reaction mixture from the reaction zone for conveyance to a subsequent process step or the performance of a subsequent step on the reaction mixture.

An additional problem occurs when reacting a mixture of branched and linear alcohols in that the reaction does not produce a mixture of branched and linear carboxylic acid salts which substantially corresponds to the alcohol mixture. The reaction tends to favor the production of linear carboxylic acid salts due to the greater activity of the linear alcohols.

All of the aforementioned problems are particularly prevalent in reacting alcohols of higher chain lengths, i.e. R equal to or greater than 5, but may be present when reacting lower chain length alcohols.

SUMMARY OF THE INVENTION AND OBJECT

It is an object of this invention to provide an improved process for producing a mixture of branched and linear carboxylic acid salts wherein foaming and/or solidification of the reaction mixture are inhibited, and the mixture of carboxylic acid salts produced substantially corresponds to the branched and linear alcohols reacted.

This invention provides for an improved process for reacting a mixture of branched and linear alcohols of the formula $RCH_2OH$ with a caustic of the formula $M(OH)_n$ to produce a reaction mixture containing carboxylic acid salts of the formula:

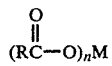

wherein: R is selected from linear alkyl and branched alkyl of from about 1 to about 19 carbon atoms and composed solely of carbon and hydrogen, M is selected from the group consisting of lithium, sodium, potassium, magnesium, calcium and barium, n is a valence factor for M, being 1 where M is selected from lithium, sodium and potassium and 2 where M is selected from magnesium, calcium and barium, and liberating hydrogen, the improvement comprising introducing into the reaction mixture at about a time when a significant evolution of hydrogen from the reaction mixture begins to occur, an effective amount of an inert diluent for the reaction mixture, wherein the effective amount is sufficient to maintain fluidity of the reaction mixture.

DETAILED DESCRIPTION OF THE INVENTION

Generally, the reaction occurs at from about 150° C. to about 350° C. in about a 1:1 molar ratio of alcohol to (—OH) groups in the $M(OH)_n$. A particular advantage of this invention is that the mixture of branched and linear carboxylic acid salts produced substantially correspond to the carbon skeletal structure and ratio of branched to linear alkyl substituents of the branched and linear alcohols reacted, being of the formula $(RCOO)_nM$.

The pressures typically involved in the reaction may range from about atmospheric pressure up to pressures of the order of 1000 to 1500 psig. and higher, particularly when there is considerable water present, as for example, where the caustic is introduced with water. The pressure may be autogenous. Atmospheric pressure is particularly preferred.

It has been found that the problems indicated previously are especially prevalent when reacting an alcohol wherein R is equal to 5 or greater and in particular when R is equal to or greater than 6, and most prevalent when R is equal to or greater than 7. The process is useful for alcohols wherein R is 19 or less. Above such carbon chain length, it is difficult (but not impossible) to find a suitable inert diluent for the reaction mixture. Preferred ranges of R are from 5 to 15 carbon atoms, 6 to 13 carbon atoms and 7 to 11 carbon atoms with the effectiveness of the process, particularly with the inert diluent exemplified herein, respectively increasing.

The mixture of branched and linear alcohols which may be used range from almost substantially pure alcohols, i.e. R is the same for both the branched and linear alcohols, to various mixtures of alcohols such as those available in various commercial mixtures. One such commercial mixture is Monsanto's OXO ALCOHOL 7911 which generally consists of about 35% branched alcohol and about 65% linear chain alcohols and about an equal mixture of 7, 9 and 11, (i.e. R is 6, 8 and 10) carbon atoms. Table I, below, describes the properties of Monsanto's OXO ALCOHOL 7911:

TABLE I

| MONSANTO OXO ALCOHOL 7911 | |
|---|---|
| Composition: | |
| Linear Alcohols | 65% min. |
| Branched Alcohols | 35% max. |
| Heptanols | 30–34% |
| Nonanols | 35–43% |
| Undecanols | 27–31% |
| Alcohol Content | 98.5% min. |
| Appearance | Clear liquid |
| Color, APHA | 8 max. |
| Specific Gravity 20°/20° C. | 0.826–0.832 |
| Refractive Index a 25° C. | 1.420–1.440 |
| Acidity (as acetic acid) | 0.03% max. |
| Aldehydes (as $C_7C_9C_{11}$) | 0.14% max. |
| Moisture | 0.1% max. |
| Boiling Point Range | 178–238° C. |
| Melting Point | −65° to −79° C. |
| Flash Point (open cup) | 190° F. |

Other similar type mixtures of branched and linear chain alcohols may also be used.

In the foregoing formula M (cation) is an alkali metal or alkaline earth metal. A preferred group consists of lithium, sodium, potassium, magnesium, calcium and barium, both individually and in various combinations, e.g. mixtures of sodium, magnesium and calcium.

In the foregoing formula for the carboxylic acid salts and in the formula for the caustic, i.e. $M(OH)_n$, n is a conventional valence factor for the metal M, being 1 for those molecules wherein M is an alkali metal such as sodium, lithium, potassium and being 2 where M is an alkaline earth metal such as calcium, magnesium and barium.

The carboxylic acid salts produced by this reaction may subsequently be acidified with mineral acid to produce the corresponding carboxylic acid.

In the reaction of the foregoing alcohols and caustic to produce the corresponding carboxylic acid salts, molecular hydrogen ($H_2$) is liberated as an off-gas at substantially the precise sites as the location of the hydroxyl groups in the starting alcohol molecules, the hydrogen being liberated in a ratio of 2 molecules thereof per molecule of starting alcohol $RCH_2OH$.

The liberation of hydrogen in the course of the caustic fusion reaction has a very definite and somewhat abrupt reaction threshold involving a fairly narrow transitional range of temperature and time, for example, from 2° to 15° C. and from 1 to 5 minutes.

This narrow transitional range is experienced even at temperatures which are quite elevated. In general, this transitional range is of such a sharp nature as to result in the virtual absence of liberation of hydrogen below the range and above the range the liberation of hydrogen continues even with the maintenance of autogenous pressure in excess of many thousands of pounds per square inch. Thus, the time when a significant evolution of hydrogen begins to occur is quite evident to one skilled in the art.

An important aspect of this forced liberation and release of hydrogen gas and other volatile materials is that the gas and volatiles bubble through the reaction mixture and along with the agitation of the reaction mixture, tend to promote foaming. If the reaction mixture has a tendency to solidify, for example, due to the production of carboxylic acid salts having a higher melting point than the reaction mixture, solid foam may be produced.

The present invention seeks to inhibit foam formation and solidification, and insure that the branched and linear mixture of carboxylic acid salts produced substantially corresponds to the branched and linear mixture of alcohols reacted, by introducing into the reaction mixture at about a time when a significant evolution of hydrogen from the reaction mixture begins to occur, an effective amount of an inert diluent for the reaction mixture. The effective amount is sufficient to maintain fluidity of the reaction mixture. The fluidity (or low viscosity) of the reaction mixture permits the escape of hydrogen and volatile materials from the reaction mixture and inhibits solidification of the reaction mixture by the dissolution or suspension of the components of the reaction mixture in the diluent. Introduction of the diluent at such a time insures that the carboxylic acid salts produced substantially correspond to the alcohols reacted.

This invention contemplates addition of the diluent somewhat before and somewhat after the onset of the liberation of hydrogen. However, optimum results are only achieved by addition at about the time of the onset of hydrogen liberation. The diluent should, preferably, not be added to the reaction mixture prior to hydrogen liberation because the diluent may effect the reaction in an adverse manner, e.g. delay the initial evolution of hydrogen thus increasing reaction times, and/or promote the formation of linear carboxylic acid salts. Addition at about the onset of the liberation of hydrogen ensures optimum results, reaction times and that the product carboxylic acid salts will substantially correspond to the starting alcohols. Addition of the diluent after the onset of hydrogen evolution does not ensure optimum results, particularly with respect to the inhibition of foaming.

The selection of the diluent depends to a large extent on the particular reactant alcohol mixture. It is essential that the diluent remain substantially liquid under the conditions of the reaction, i.e. have a low volatility at the temperatures and pressures of reaction. Additionally, the diluent should not polymerize and/or degrade at the temperatures and pressures of reaction. It is highly desirable that the diluents be capable of separation from the reaction mixture after the reaction is complete or after subsequent reaction steps, either by distillation or phase separation. Preferably, the diluent may be recovered by, for example, phase separation or distillation, for reuse.

A preferred diluent is a mineral oil. The mineral oils which may be employed in carrying out the instant invention are well known in the art. The preferred mineral oils for use in this invention are SOLTROL 170 by Phillips Petroleum Company, Inc., Bartletsville, Okla., U.S.A. Table II, below, describes the properties of SOLTROL 170.

TABLE II

SOLTROL 170 FROM PHILLIPS CHEMICAL COMPANY
Hydrocarbon Mixture of $C_{13-14}$ Isoparaffins

| PROPERTY | TYPICAL | SPECIFICATION MINIMUM | SPECIFICATION MAXIMUM | TEST METHOD |
|---|---|---|---|---|
| Distillation, rec., F. at 760 | | | | ASTM D 86 |
| IBP | 423 (217° C.) | 420 | — | |
| 10% | 431 | — | — | |
| 50% | 438 | 430 | 450 | |
| 90% | 453 | — | — | |
| EP | 468 (242° C.) | 450 | 475 | |
| Specific Gravity, 60/60F. | 0.785 | — | — | ASTM D 1298 |
| Density at 60 F., lb/gal | 6.53 | — | — | ASTM D 1250 |
| Bromine Number | 1.8 | — | — | ASTM D 1159 |
| Flash Point, F. | 185 | 175 | — | ASTM D 56 |
| Saybolt Color | 30 | 25 | — | ASTM D 156 |
| Sulfur Content, wt. percent | 0.0010 | — | — | ASTM D 1266 |
| Acidity of Distillation Residue | Neutral | Neutral | Neutral | ASTM D 1093 |
| Aniline Point, F. | 192 | 190 | — | ASTM D 1012 |
| Copper Corrosion, 3 hrs. at 212 F. | 1 | — | 1 | ASTM D 130 |
| Kauri-Butanol Value | 24.6 | — | — | ASTM D 1133 |
| Kinematic Viscosity, cs at 100 F. | 2.51 | — | — | ASTM D 445 |

An effective amount of the inert diluent for the reaction mixture must be utilized. This amount is an amount which is sufficient to maintain fluidity (low viscosity) of the reaction mixture to allow passage therethrough of the hydrogen liberated therefrom, and to sufficiently fluidize the reaction mixture after the reaction is complete and in subsequent process steps performed thereon, to prevent solidification. The optimum amount being employed at any particular instance to achieve such results can be readily determined. The optimum amount of diluent employed will depend on the particular reaction mixture, i.e. alcohol, caustic, catalyst, etc., being treated, the particular diluent employed, and the reaction conditions. It has been found that a range of from about 5% to about 100% by weight of the reaction mixture can be employed. A particularly preferred range is from about 20% to about 80% by weight.

The process of this invention has been found particularly useful in inhibiting foaming and solidification of the reaction mixture wherein the alcohol reacted is, for example, Monsanto's 7911 alcohol, and ensuring that the carboxylic acid salts produced substantially correspond to the alcohols reacted.

The mechanism by which the instant process achieves the desired results is not definitely understood. It is believed, however, that the diluent employed herein decreases the viscosity of the reaction mixture to allow for the escape of hydrogen therefrom in such a manner as to reduce foaming caused by such hydrogen liberation and to reduce the quantity of hydrogen entrapped in the reaction mixture; and/or the diluent dissolves the reaction mixture, which may be predominately carboxylic acid salt, to prevent solidification thereof.

Additionally, the addition of the diluent at the specific time indicated, rather than earlier, permits both the branched and linear alcohols to react with the dissolved caustic prior to introduction of the diluent, thus not preferring the formation of linear salts which would occur if the diluent was added earlier.

It has been found that this process is particularly useful when a catalyst is used to promote the reaction of the alcohols and caustic. Such catalysts are described for example in U.S. Pat. No. 3,957,838 (metallic zinc or zinc compound), U.S. Pat. No. 3,910,973 (titanium dioxide), U.S. Pat. No. 3,864,369 (zinc and solid carbon), U.S. Pat. No. 3,717,676 (cadmium), U.S. Pat. No. 3,657,293 (co-catalyst system), U.S. Pat. No. 3,449,413 (copper oxide or hydroxide, etc.), U.S. Pat. No. 3,365,476 (solid carbon), U.S. Pat. Nos. 2,384,817 and 2,696,501 (cadmium) and are well known in the art. The entire disclosures of all of these references are incorporated herein by reference. A preferred catalyst for use in the process of this invention is zinc oxide (ZnO) whose use is exemplified in U.S. Pat. No. 3,957,838. This catalyst may be used at both atmospheric and above atmospheric pressures.

The following examples are illustrative of the invention and are not to be regarded as limitative.

COMPARATIVE EXAMPLE I

NO DILUENT

Equipment

Reaction Vessel

A one-liter three-neck, glass round-bottom flask was used as the reaction vessel. In the center neck a simple glass paddle design blade with glass rod stirrer was connected to a variable high speed stirrer motor. On another neck a "Y" shaped adapter was placed to allow for a thermometer for measuring the reaction mixture temperature and an addition funnel containing water. The addition funnel had a side arm with stopcock. The addition funnel was also equipped with nitrogen inlet for purging both the funnel and the reaction vessel.

On the other neck was placed another "Y" shaped adapter. On this adapter was fitted a thermometer to measure vapor temperatures and a Dean Stark trap with condenser. The Dean Stark trap had provisions for draining bottom layers (water in this case) and also for recycle of the lower portion into the reaction flask (total reflux).

The condenser outlet on the Dean Stark trap led to a container to catch any foam or liquids uncondensed by the condenser. The foam container was connected by a tee to a positive nitrogen source and a Precision Scientific Wet test meter. The meter gave both total gas evolution and instantaneous gas evolution rates. The wet test flowmeter also served to isolate the system from air and prevent flashbacks in the event of hydrogen ignition. The exit port from the wet test meter was to an exhaust hood.

Heat Bath

Oil was used as the heat transfer agent. A 600 watt thermowatch heat source for the oil was supplemented when necessary with a hot plate type heater-stirrer. A high grade silicon oil with a flash point of 315° C. was the heat transfer agent in the bath.

REACTANTS

Monsanto OXO Alcohol 7911 alcohol
Technical grade sodium hydroxide flakes
Reagent grade zinc oxide powder
Reagent grade calcium hydroxide powder
Magnesium hydroxide powder

Comparative Process

Into the reaction vessel was placed 388.8 g of Monsanto's 7911 alcohol (2.69 mole). While stirring, 122.4 g of sodium hydroxide (2.97 mole), 3.9 g of zinc oxide, 5.9 g of calcium hydroxide and 5.9 g of magnesium hydroxide were then added to the vessel. The vessel was sealed and purged with nitrogen and water was placed in the addition funnel and heating commenced. After initial water removal to initiate reaction, an attempt was made to control the reaction by adding water back from the addition funnel. Table III shows the course of the reaction with time zero being when vapors first distilled. At 25 minutes it was noted that the flask was 63% full and at 40 minutes the onset of foaming occurred. The flask was 75% full. Increasing stirring speed helped reduce the foam somewhat, but not completely. At 47 minutes the flask was almost completely filled with foam. Addition of water was commenced in an attempt to control the foam. At 51 minutes the foam had gone down some but the flask was still 88% full. At 61 minutes the flask was again filled with foam. At 83 minutes the foam appeared to subside but reappeared at 96 minutes. A few minutes later, the foam increased to fill the entire apparatus. The foam solidified in cooler parts of the apparatus blocking the escape of hydrogen. At this point the clamped ball joints of the reactor connected to the rest of the apparatus separated. Hydrogen and foam then came out of the separated ball joints. Since approximately 120 liters of hydrogen would be liberated by the reaction at standard temperature and pressure, we had completed approximately 67% of reaction (81 liters). The reaction was terminated.

TABLE III

| Time (min) | Oil Temp. (°C.) | Reactor Temp. (°C.) | Vapor Temp. (°C.) | Total $H_2O$ Out (Ml.) | Total $H_2O$ In (Ml.) | $H_2$ Rate (l/hr.) | $H_2$ Total (l) |
|---|---|---|---|---|---|---|---|
| 0 | 237 | 182 | 97 | 0 | 0 | 0 | 0 |
| 7 | 240 | 186 | 154 | 6.0 | 0 | 4 | 0.8 |

TABLE III-continued

| Time (min) | Oil Temp. (°C.) | Reactor Temp. (°C.) | Vapor Temp. (°C.) | Total H$_2$O Out (Ml.) | Total H$_2$O In (Ml.) | H$_2$ Rate (l/hr.) | H$_2$ Total (l) |
|---|---|---|---|---|---|---|---|
| 15 | 249 | 189 | 156 | 9.2 | 0 | 4 | 1.5 |
| 25 | 253 | 192 | 154 | 12.6 | 0 | 22 | 4.8 |
| 40 | 258 | 192 | 135 | 15.2 | 0 | 34 | 14.0 |
| 47 | 261 | 190 | 136 | 15.6 | 0 | 52 | 18.9 |
| 51 | 265 | 189 | 133 | 15.6 | 0 | 36 | 22.8 |
| 57 | 267 | 191 | 132 | 15.6 | 3.0 | 36 | 26.0 |
| 61 | 259 | 191 | 133 | 15.6 | 3.0 | — | 28.0 |
| 67 | 249 | 192 | — | 15.6 | 3.0 | 48 | 32.0 |
| 83 | 241 | 189 | 125 | 15.6 | 14.6 | 63 | 45 |
| 96 | 241 | 190 | 122 | 15.6 | 14.6 | 87 | 61.5 |
| — | — | — | — | — | — | — | 81 |

COMPARATIVE EXAMPLE II

Diluent Introduced at Beginning of Reaction

The equipment described in Comparative Example I was charged with Monsanto's 7911 alcohol (260 g) and Soltrol 170 (96 g). Sodium hydroxide flake (81 g), magnesium hydroxide (3.9 g), calcium hydroxide (3.9 g) and zinc oxide (2.6 g) was added to the stirring mixture. The reactor was sealed and stirring maintained at 200 RPM. Heat was applied. When the mixture reached a temperature of 194° C. distillate began collecting in the phase separator. The organic layer was returned to the reaction mixture while the water was collected. After 8.0 ml of water collected, the hydrogen evolution rate had risen from 0 to 320 cc/min. and the reaction temperature was now 202° C. Small increments of water were added back to the mixture over the next 3 hours in order to maintain the hydrogen evolution rate at 300–800 cc/min. The total amount of water added was 8.0 ml. Only 85% of the theoretical amount of hydrogen evolved.

Very little foaming occurred. A small portion (10 g) of soap mixture was withdrawn from the reactor at this point and acidified carefully with 25 ml of concentrate a hydrochloric acid. The organic phase was separated, dried over magnesium sulfate, anhydrous, and analyzed by gas chromatography. The analysis mixture contained 24% branched acid.

After an additional 6 hours of heating the reaction mixture was reanalyzed as above and found to still contain 24% branched acid.

The Monsanto 7911 alcohol used had analyzed composition of 30% branched and 70% linear alcohol.

EXAMPLE 1

The equipment described in Example 2 was charged with Monsanto 7911 alcohol (260 g). Sodium hydroxide (81 g), magnesium hydroxide (3.9 g), calcium hydroxide (3.9 g) and zinc oxide (2.6 g) were added to the stirring mixture. The reactor was sealed, stirring maintained at 200 RPM, and heat applied. Distillate began collecting at 183°. The organic phase was returned to the reactor and the water removed. After 5.0 ml of water was removed, Soltrol 170 (96 g) was added over a 30 minute period. During the addition of the Soltrol, hydrogen evolution began and increased to 520 cc/min. An additional 4.3 g of water was removed during this period. After the Soltrol was added, water was added dropwise in order to maintain a rate of hydrogen evolution of 500 cc/min. After 2 hours the hydrogen evolution rate had fallen to 10 cc/min and the reaction had ceased. The temperature was now 215°. Steam was passed through the reaction slowly in order to maintain a temperature above 180°. Soltrol and unreacted alcohol were removed by codistillation with water. After the total amount of Soltrol was collected, water was allowed to accumulate in the reactor to dissolve the soap. The resulting solution was acidified to give a mixture of carboxylic acids containing 29% branched acid.

What is claimed is:

1. In a process for reacting a mixture of branched and linear alcohols of the formula RCH$_2$OH with a caustic of the formula M(OH)$_n$ producing a reaction mixture containing carboxylic acid salts of the formula:

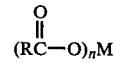

wherein:
  R is selected from linear alkyl and branched alkyl of from about 1 to about 19 carbon atoms and composed solely of carbon and hydrogen,
  M is selected from the group consisting of lithium, sodium, potassium, magnesium, calcium and barium, n is a valence factor for M, being 1 where M is selected from lithium, sodium and potassium and 2 where M is selected from magnesium, calcium and barium,
  and liberating hydrogen, the improvement comprising introducing into the reaction mixture at about a time when a significant evolution of hydrogen from the reaction mixture begins to occur, an effective amount of an inert diluent for the reaction mixture, wherein the effective amount is sufficient to maintain fluidity of the reaction mixture.

2. The process of claim 1, wherein R is from 5 to 15 carbon atoms.

3. The process of claim 1, wherein R is from 6 to 13 carbon atoms.

4. The process of claim 1, wherein R is from 7 to 11 carbon atoms.

5. The process of claim 1, wherein the caustic is sodium hydroxide.

6. The process of claim 1, wherein the diluent is a mineral oil.

7. The process of claim 1, wherein the effective amount is from about 5% to about 100% by weight of the reaction mixture.

8. The process of claim 1, wherein the effective amount is from about 20% to about 80% by weight of the reaction mixture.

9. The process of claim 1, wherein the reaction takes place in the presence of an effective amount of a catalyst.

10. The process of claim 9, wherein the catalyst is ZnO.

* * * * *